United States Patent
Kinder, Jr.

(10) Patent No.: US 6,506,910 B1
(45) Date of Patent: Jan. 14, 2003

(54) PROCESS FOR PREPARING DISCODERMOLIDE AND ANALOGUES THEREOF

(75) Inventor: Frederick Ray Kinder, Jr., Morristown, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/922,055

(22) Filed: Aug. 3, 2001

Related U.S. Application Data

(60) Provisional application No. 60/325,767, filed on Aug. 7, 2000.

(51) Int. Cl.[7] .................... C07D 407/00; C07D 309/30; C07D 239/00; C07D 233/00

(52) U.S. Cl. .................. 549/273; 549/292; 549/293; 564/161; 564/164; 564/192; 564/193; 564/197

(58) Field of Search ................................. 549/273, 292, 549/293; 564/161, 162, 192, 193, 197

(56) References Cited

FOREIGN PATENT DOCUMENTS

| GB | 2280677 | 2/1995 |
|----|---------|--------|
| WO | WO 98/24429 | 6/1998 |
| WO | WO 00/04865 | 2/2000 |

OTHER PUBLICATIONS

Paterson, et al., Agnew. Chem., Int. Ed., vol. 39, No. 2, "Total Synthesis of the Antimicrotubule Agent (+)–Discodermolide Using Boron–Mediated Aldol Reactions of Chiral Ketones", pp. 377–380 (2000).

Filla, et al., Tetrahedron Letters, vol. 40, No. 30, "Synthesis of C1–C8 and C9–C24 fragments of (−)–discodermolide; use of asymmetric alkylation and stereoselective aldol reactions", pp. 5449–5453 (1999).

Harried, et al., J. Org. Chem., vol. 62, "Total Synthesis of (−)–Discodermolide: An Application of a Chelation–Controlled Alkylation Reaction", pp. 6098–6099 (1997).

Marshall, et al., J. Org. Chem., vol. 63, No. 22, "Total Synthesis of (+)–Discodermolide" pp. 7885–7892 (1998).

Smith, et al., Org. Lett. , vol. 1, No. 11, "Gram–Scale Synthesis of (+)–Discodermolide", pp. 1823–1826 (1999).

Hung et al., J. Am. Chem. Soc., vol. 118, No. 45, "Syntheses of Discodermolides Useful for Investigating Microtubule Binding and Stabilization", pp. 11054–11080 (1996).

Smith, et al., J. Am. Chem. Soc., vol. 117, No. 48, "Total synthesis of (−)–Discodermolide", pp. 12011–12012 (1995).

Halstead, UMI No. 9921509 "II. Total synthesis of (−)–discodermolide, pp. 92–152, III. Total synthesis of (+)–discodernmolide", pp. 153–199, (1999).

*Primary Examiner*—Amelia Owens
(74) *Attorney, Agent, or Firm*—Joseph J. Borovian

(57) ABSTRACT

A more practical synthesis for preparing discodermolide and structurally related analogues, novel compounds useful in the process and novel compounds prepared by the process.

16 Claims, No Drawings

PROCESS FOR PREPARING DISCODERMOLIDE AND ANALOGUES THEREOF

This application claims the benefit of U.S. Provisional Application No. 60/325,767, filed Aug. 7, 2000, which was converted from U.S. application Ser. No. 09/633,753, and which is incorporated herein by reference.

The invention relates to a process for preparing discodermolide and analogues thereof, to novel compounds utilized in the process and to novel compounds prepared by the process.

FIELD OF INVENTION

The present invention relates to the area of synthetic methodology and, more particularly, to a process for preparing discodermolide and analogues thereof.

BACKGROUND OF THE INVENTION

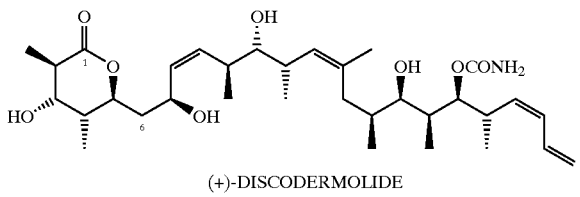

(+)-DISCODERMOLIDE (+)-Discodermolide is a novel polyketide natural product that was isolated from extracts of the marine sponge *Discodermolide dissoluta* by researchers at the Harbor Branch Oceanographic Institution (HBOI) (Gunasekera S P, Gunasekera M, Longley R E, Schulte G K. Discodermolide: a new bioactive polyhydroxylated lactone from the marine sponge *Discodernia dissolute*. [published erratum appears in J. Org. Chem. 1991;56:1346]. J. Org. Chem. 1990;55:4912–15.). Discodermolide lacks obvious structural resemblance to paclitaxel, yet it shares with paclitaxel (the active substance in the drug Taxol) the ability to stabilize microtubules. In mechanism-based assays, discodermolide is more effective than paclitaxel. In fact, of the handful of compounds known to induce polymerization of purified tubulin, discodermolide is the most potent. However, microtubules, a major structural component in cells, are not simple equlibrium polymers of tubulin. They exist as regulated GTP-driven dynamic assemblies of heterodimers of a and P tubulin. Although the dynamics are relatively slow in interphase cells, upon entering mitosis, the rate of growing and shortening increases 20 to 100-fold—the average microtubule turns over half the tubulin subunits every ten seconds. This change in rate allows the cytoskeletal microtubule network to dismantle and a bipolar spindle-shaped array of microtubules to assemble. The spindle attaches to chromosomes and moves them apart. The response to complete suppression of microtubule dynamics in cells is death. However, mitotic cells are more sensitive and the tolerance threshold appears to be cell-type specific. Molecules like paclitaxel that bind with high affinity to microtubules disrupt the dynamics process in tumor cells with lethal results even when the ratio of bound drug to tubulin is very low. Discodermolide binds to tubulin competitively with paclitaxel. Since paclitaxel has proven to be useful in treating some cancers, other compounds of the same mechanistic class may have utility against hyperproliferative disorders.

Future development of discodermolide or structurally related analogues is hindered by the lack of a reliable natural source of the compound or a feasible synthetic route. Naturally occurring discodermolide is scarce and harvesting the producing organism presents logistical problems. Accordingly, there is an ever-growing need for improved syntheses which enable the preparation of commercially acceptable quantities of discodermolide and structurally related analogues.

DESCRIPTION OF THE PRIOR ART

WO 00/04865 discloses the preparation of intermediates for the synthesis of discodermolide and their polyhydroxy dienyl lactone derivatives for pharmaceutical use.

Agnew. Chem., Vol. 39, No. 2, pgs. 377–380 (2000) discloses the total synthesis of the antimicrotubule agent (+)-discodermolide using boron-mediated aldol reactions of chiral ketones.

Org. Lett., Vol. 1, No. 11, pgs. 1823–1826 (1999) discloses the gram-scale synthesis of (+)-discodermolide.

Diss. Abstr. Int., Vol. 60, No. 3, pg. 1087 (1999) discloses the total synthesis of (+)-miyakolide, (–)-discodermolide and (+)-discodermolide.

Tetrahedron Lett., Vol. 40, No. 30, pgs 5449–5453 (1999) discloses the synthesis of C1–C8 and C9–C24 fragments of (–)-discodermolide.

Diss. Abstr. Int., Vol. 59, No. 11, pg. 5854 (1999) discloses a total synthesis of (–)-discodermolide.

J. Org. Chem., Vol. 63, No. 22, pgs. 7885–7892 (1998) discloses the total synthesis of (+)-discodermolide.

WO 98/24429 discloses synthetic techniques and intermediates for polyhydroxy, dienyllactones and mimics thereof.

J. Am. Chem. Soc., Vol. 118, No. 45, pgs. 11054–11080 (1996) discloses the syntheses of discodermolides useful for investigating microtubule binding and stabilization.

J. Am. Chem. Soc., Vol. 117, No. 48, pgs. 12011–12012 (1995) discloses the total synthesis of (–)-discodermolide.

British Patent Application 2,280,677 discloses the total synthesis of discodermolide.

SUMMARY OF THE INVENTION

The present invention relates to a more practical synthesis of discodermolide and analogues thereof. In another embodiment, the instant invention relates to novel compounds useful in the preparation of discodermolide and analogues thereof. In a further embodiment, the instant invention relates to novel compounds which are prepared by the process of the instant invention.

DETAILED DESCRIPTION OF THE INVENTION

The essence of the instant invention is the discovery of a more practical synthesis for discodermolide and analogues thereof. More particularly, it has been discovered that discodermolide and analogues thereof can be prepared by a three-step reaction as follows:

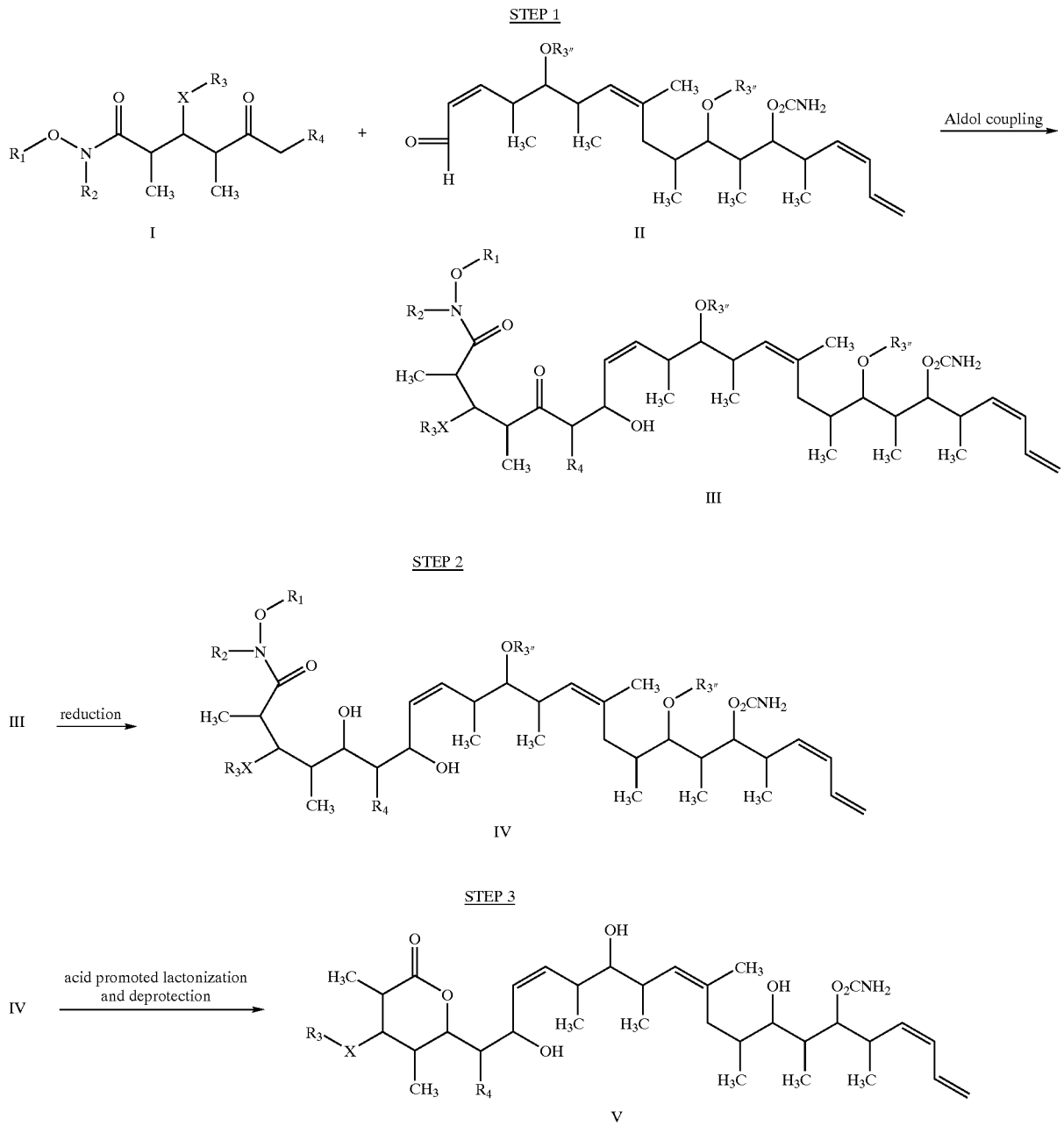

where $R_1$ is $(C_{1-6})$ alkyl, benzyl or an acid labile hydroxyl protecting group; $R_2$ is $(C_{1-6})$ alkyl or benzyl; $R_3$ is hydrogen, $(C_{1-6})$ alkyl, benzyl, $C(O)(C_{1-12})$ alkyl, $C(O)Ph$, $C(O)O(C_{1-12})$ alkyl, $C(O,Ph, C(O)NH(C_{1-12})$ alkyl, $C(O)$ NHPh or an acid labile hydroxyl protecting group; $R_3''$ is an acid labile hydroxyl protecting group; $R_4$ is hydrogen or methyl; and X is O, NH, $NCH_3$, S or $CH_2$, with the proviso that when X is O and $R_3$ is an acid labile hydroxyl protecting group in the compound of formula I, the "—X—$R_3$" moiety in the compound of formula V is —OH.

As to the individual steps, Step 1 involves the coupling of a ketone compound of formula I with an aldehyde compound of formula II via an aldol reaction to obtain a β-hydroxyketone compound of formula III. The coupling is conveniently carried out with between 1 and 20, preferably between 5 and 15, equivalents of the ketone compound of formula I relative to the aldehyde compound of formula II.

The coupling is conducted in the presence of: 1) a dialkylboron halide or triflate, preferably a chiral boron chloride or triflate, more preferably β-chlorodiisopinocamphenylborane; 2) a base, preferably an amine, more preferably triethylamine; and 3) a polar organic solvent, preferably an ether, more preferably diethyl ether, at a temperature of between −100° C. and 20° C., preferably between −78° C. and −20° C., for a period of between 2 and 72 hours, preferably for 16 hours.

Step 2 concerns the reduction of the β-hydroxyketone compound of formula III and, more particularly, the ketone group common to such compounds, to obtain a 1,3-diol compound of formula IV. The reduction is conducted in the presence of: 1) a ketone reducing agent, preferably a borohydride such as tetramethylammonium triacetoxyborohydride; 2) a polar organic solvent, preferably acetonitrile; and 3) a protic solvent, preferably a carboxylic acid, such as acetic acid, at a temperature of between −78° C. and 20° C., preferably between −40° C. and −10° C., for a period of between 2 and 72 hours, preferably for 16 hours.

As to Step 3, it involves the lactonization and deprotection of the acid labile hydroxyl protecting groups of a compound of formula IV to obtain a compound of formula V. The lactonization and deprotection reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, more preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

In another embodiment, the instant invention relates to the novel ketone compounds of formula I:

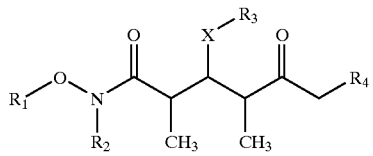

I where $R_1$ is $(C_{1-6})$ alkyl, benzyl, or an acid labile hydroxyl protecting group;

$R_2$ is $(C_{1-6})$ alkyl, or benzyl;

$R_3$ is hydrogen, $(C_{1-6})$ alkyl, benzyl, $C(O)(C_{1-12})$ alkyl, $C(O)Ph$, $C(O)O(C_{1-12})$alkyl, $C(O)OPh$, $C(O)NH(C_{1-12})$alkyl, $C(O)NHPh$, or an acid labile hydroxyl protecting group;

$R_4$ is hydrogen or methyl; and

X is O, NH, $NCH_3$, S or $CH_2$.

Preferred compounds are those of formula Ia:

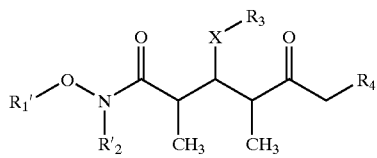

Ia where each of $R_1'$ and $R_2'$ is $(C_{1-6})$ alkyl;

X is O, or $CH_2$; and $R_3$ and $R_4$ are as defined above.

More preferred compounds are those of formula Ib:

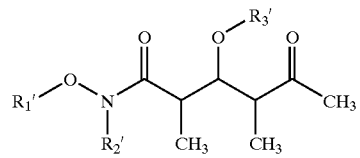

Ib where $R_3'$ is $(C_{1-6})$alkyl, $C(O)(C_{1-12})$alkyl, benzyl, $C(O)O(C_{1-12})$alkyl, or an acid labile hydroxy protecting group; and $R_1'$ and $R_2'$ are as defined above.

Even more preferred compound are those of formula Ic:

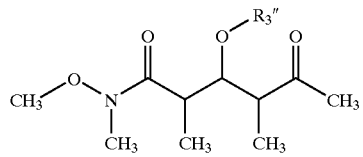

Ic where $R_3''$ is an acid labile hydroxyl protecting group.

In the above definitions: the term "$(C_{1-6})$ alkyl" as used herein refers to a straight or branched chain group consisting solely of carbon and hydrogen and having from 1 to 6 carbon atoms, whereas the term "$(C_{1-12})$ alkyl" as used herein refers to a straight or branched chain group consisting solely of carbon and hydrogen and having from 1 to 12 carbon atoms. Examples of "alkyl" groups include methyl, ethyl, propyl, butyl, pentyl, 3-methylpentyl, etc.

The term "acid labile hydroxyl protecting groups" as used herein refers to any oxygen bound group that can be removed upon exposure to an acid. Numerous examples of these groups are known by those skilled in the art and can be found in Greene and Wuts, Protective Groups in Organic Synthesis, 2d edition, John Wiley & Sons, New York, 1991. Specific examples include, but are not limited to, t-butyldimethylsilyl, triethylsilyl, t-butyldiphenylsilyl, triisopropylsilyl, methoxymethyl, and tetrahydropyranyl.

In a further embodiment, the instant invention relates to a process for preparing the novel compounds of formula I. More particularly, the compounds of formula I may be prepared as depicted below:

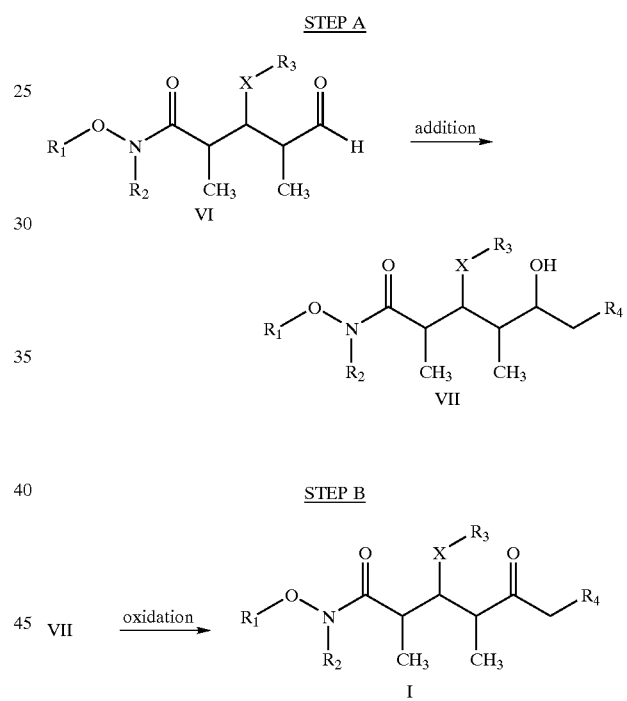

where $R_1$, $R_2$, $R_3$, $R_4$ and X are as defined above.

As to the individual steps, Step A involves the addition of a methyl or ethyl group to an aldehyde compound of formula VI to obtain an alcohol compound of formula VII. The addition is carried out in the presence of: 1) an organometallic reagent, preferably an alkyllithium or alkylmagnesium halide such as methylmagnesium bromide; and 2) a polar organic solvent, preferably an ether such as diethyl ether, at a temperature of between −78° C. and 40° C., preferably at −78° C. and 0° C., more preferably at about −40° C., for a period of between 5 minutes and 24 hours, preferably between 30 minutes and 2 hours, more preferably for about 1 hour.

Step B involves the oxidation of an alcohol compound of formula VII to obtain the desired ketone compound of formula I. The oxidation is carried out in the presence of: 1) an oxidant, preferably a combination of dimethylsulfoxide and an activating agent, more preferably a combination of dimethylsulfoxide and sulfur trioxide complex with pyridine; 2) a base, preferably an organic base, more preferably a trialkylamine such as triethylamine; and 3) a polar organic solvent, preferably a chlorinated hydrocarbon such as dichloromethane. The oxidation is suitably carried out a temperature of between −78° C. and 40° C., preferably between 5° C. and 20° C., for a period of between 5 minutes and 24 hours, preferably between 1 hour and 12 hours, more preferably between 4 and 6 hours.

The aldehyde compounds of formulae II and VI are either known or may be prepared analogous to processes set forth in the literature for other structurally similar aldehydes.

In still another embodiment, the instant invention relates to the novel β-hydroxyketone compounds of formula III and the novel 1,3-diol compounds of formula IV.

Although the product of each reaction described above may, if desired, be purified by conventional techniques such as chromatography or recrystallization (if a solid), the crude product of one reaction is advantageously employed in the following reaction without purification.

As is evident to those skilled in the art, compounds of formulae I and III–V contain asymmetric carbon atoms and, therefore, it should be understood that the individual stereoisomers are contemplated as being included within the scope of this invention.

The following examples are for purposes of illustration only and are not intended to limit in any way the scope of the instant invention.

EXAMPLE 1

Preparation of (2R,3S,4R)-3-[[(1,1-dimethylethyl)dimethylsilyl]oxy]-N-methoxy-N,2,4-trimethyl-5-oxo-hexanamide

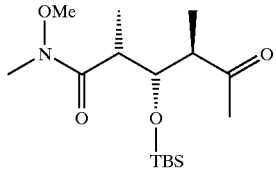

a) Preparation of (2R,3S,4S)-3-[[(1,1-Dimethylethyl)dimethylsilyl]oxy]-5-hydroxy-N-methoxy-N,2,4-trimethyl-hexanamide

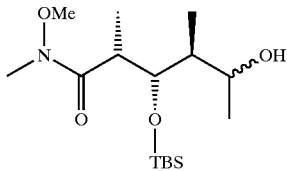

To a solution of 6.9 g (21.8 mmol) of (2R,3S,4R)-3-[[(1,1-dimethylethyl)dimethylsilyl]oxy]-N-methoxy-N,2,4-trimethyl-5-oxo-pentanamide in 50 mL of ether is added 10.2 mL (30.5 mmol) of a 3M solution of methylmagnesium bromide in ether, dropwise, at −40° C., after which the mixture is stirred at −20° C. for 1 hour. The reaction mixture is then dilluted with 200 mL of ether and the reaction is quenched by adding the reaction mixture to 20 g of crushed ice at 0° C. The mixture is then washed with 100 mL of 1 M sodium hydrogen sulfate solution and partitioned with two 150 mL portions of ether. The organic layers are then combined and dried over sodium sulfate. The crude product mixture is then chromatographed employing an eluent mixture of 20% ethyl acetate in hexane initially and then an eluent mixture of 40% ethyl acetate in hexane to yield two diastereomers as light yellow oils which are used in the next step without further purification.

Diastereomer 1: $^{1}$H NMR(300 MHz, CDCl$_3$): δ4.08 (dd, J=9.8, 6.8 Hz, 2H), 3.64 (s, 3H), 3.54 (d, J=2.6 Hz, 2H), 3.08 (s, 3H), 3.00 (m, 2H), 1.48 (m, 2H), 1.07 (d, J=6.8 Hz, 3H), 1.05 (d, J=6.4 Hz, 3H), 0.81 (s, 9H), 0.76 (d, J=7.2 Hz, 2H), 0.01 (d, J=3.8 Hz, 6H). Diastereomer 2: $^{1}$H NMR(300 MHz, CDCl$_3$): δ 4.19 (dd, J=12.1, 6.0 Hz, 2H), 3.86 (dd, J=9.0, 1.51 Hz, 2H), 3.56 (s, 3H), 3.18 (m, 2H), 3.01 (s, 3H), 1.28 (m, 2H), 1.06 (d, J=6.8 Hz, 3H), 0.94 (d, 6.4 Hz, 3H), 0.88 (d, 7.2 Hz, 3H), 0.78 (s, 9H), 0.01 (d, 1.3 Hz, 6H).

b) Preparation of the Title Compound

To a solution of 13.1 g (39.5 mmol) of the diastereomeric mixture prepared in a) above in a mixture comprising 150 mL of methylene chloride, 50 mL of dimethylsulfoxide and 25 mL of triethylamine is added, dropwise via an addition funnel, 19.0 g (120 mmol) of sulfur trioxide pyridine complex in 150 mL of dimethylsulfoxide at 0° C. The resultant solution is then stirred for 1½ hours at 0° C., after which time the reaction mixture is concentrated via a rotary evaporator in a cooling both at <10° C. The solution is then diluted with 200 mL of ether, and then extracted successively with 200 mL of a 1 M sodium hydrogen sulfate solution and 200 mL of brine. The organic layer is then dried over sodium sulfate and the crude product mixture is purified by flash chromatography employing hexane as the eluent initially and then an eluent mixture of 5% ethyl acetate in hexane to yield the desired compound as a clear oil. $^{1}$H NMR (300 MHz, CDCl$_3$) δ 4.23 (dd, J=7.5, 4.2 Hz, 2H), 3.61 (s, 3H), 3.01 (s, 3H), 2.92 (m, 2H), 2.64 (m, 2H), 2.08 (s, 3H), 1.03 (d, J=6.8 Hz, 3H), 0.98 (d, J=7.2 Hz, 3H), 0.81 (s, 9H), 0.00 (s, 6H).

EXAMPLE 2

Preparation of (+)-discodermolide

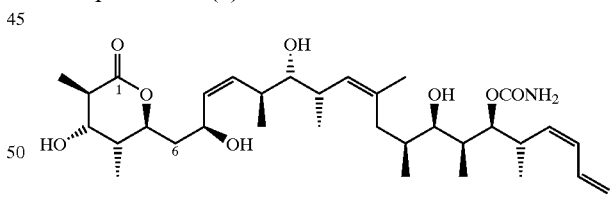

a) Preparation of (2R,3S,4R,7S,8Z,10S, 11S,12S,13Z,16S, 17R,18R,19S,20S, 21E)-19-[(Aminocarbonyl)oxyl]-3,11, 17-tris[[(1,1-dimethylethyl)dimethylsilyl]oxy]-7-hydroxy-N-methoxy-N,2,4,10,12,14,16,18,20-nonamethyl-5-oxo-8,13,21,23-tetracosatetraenamide

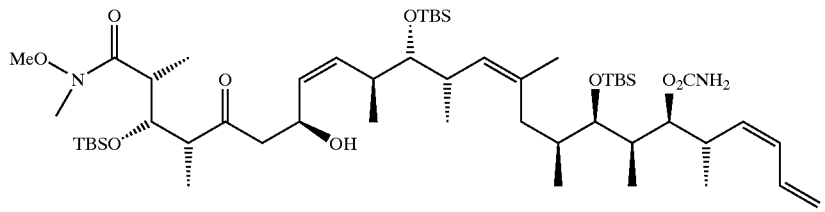

To a stirred solution of 2.18 g (6.79 mmol, 10 equiv.) of (+)-β-chlorodiisopinocamphenylborane in 4 mL of diethyl ether at 0° C. is added 1.04 mL (11 equiv., distilled over calcium hydride) of triethylamine and then a solution of 2.25 g (6.79 mmol, 10 equiv.) of the compound of Example 1 in 3 mL of diethylether. After stirring for 2 hours at 0° C., the mixture is cooled to −78° C., after which time a pre-cooled (−78° C.) solution of 450 mg (0.679 mmol) of (2Z,4S,5S, 6S,7Z,10S,11R,12R,13S,14S,15E)-13-[(amino-carbonyl) oxyl]-5,11-bis[[(1,1-dimethylethyl)dimethylsilyl]oxy]-4,6, 8,10,12,14-hexamethyl-2,7,15,17-octadecatetraenal in 4 mL of diethylether is added via cannula. After the resultant mixture is maintained at a temperature of −78° C. for 3 hours, it is transferred to a freezer (−27° C.) for 16 hours. The reaction is then quenched with 8 mL of methanol (the pH of which is adjusted to 7 with 12 mL of buffer solution) and 4 mL of 50% hydrogen peroxide solution at 0° C. After stirring for 2 hours at 25° C., the organic layers are separated. The aqueous layer is then extracted five times with 25 mL portions of dichloromethane. The combined organic layers are then dried over magnesium sulfate, concentrated using a rotary evaporator and chromatographed (Biotage, silica gel, gradient 10–30% ethyl acetate/hexane) to yield the desired compound as a colorless, highly viscous oil.

$[\alpha]_D$+12.56° (c=1.0, $CH_2Cl_2$); IR ($CH_2Cl_2$) 3547 (m, OH), 3359 (m, $CONH_2$), 2958 (vs), 2990 (vs), 1729 (vs, C=O), 1664 (m), 1462 (s), 1385 (s), 1254(s), 1037 (s), 1037 (s), 1004 (s), 835 (vs); $^1H$ NMR (500 MHz, $CDCl_3$) δ 6.61 (1 H, ddd, J=17.1, 10.5, 10.5 Hz, $H_{23}$), 6.03 (1H, dd, J=11.0, 11.0 Hz, $H_{22}$), 5.50 (1H, dd,J=10.6, 10.6 Hz, $H_9$), 5.37 (1H, dd, J=10.6, 10.5 Hz, $H_{21}$), 5.35 (1H, dd, J=10.8, 8.5 Hz, $H_8$), 5.23 (1H, dd, J=15.3, 2.1 Hz, $H_{24A}$), 5.13 (1H, d, J=10.2 Hz, $H_{24B}$), 5.05 (1H, d, J=10.0 Hz, $H_{13}$), 4.79 (1H, t, J=8.0 Hz, $H_7$), 4.72 (1H, t, J=5.9 Hz, $H_{19}$), 4.60–4.50 (2H, br, CON$\underline{H}_2$), 4.33 (1H, dd, J=6.9, 4.3 Hz, $H_3$), 3.74 (3H, s, NOC$\underline{H}_3$), 3.43 (1H, dd, J=5.0, 4.1 Hz $H_{17}$), 3.31 (1H, dd, J=5.2, 5.1 Hz, $H_{11}$), 3.13 (3H, s, $NCH_3$), 3.08 (1H, br, OH), 3.00 (1H, m, $H_{20}$), 2.78–2.69 (2H, m, $H_4$+$H_{6A}$), 2.70–2.62 (1H, m, $H_{10}$), 2.66–2.54 (2H, m, $H_2$+$H_{6B}$), 2.49–2.45 (1H, m, $H_{12}$), 2.12(1H, dd, J=12.4, 12.3 Hz, $H_{15A}$), 1.93–1.86 (2H, m, $H_{16}$+$H_{18}$), 1.76–1.65 (1H, m, H15B), 1.62 (3H, s, $Me_{14}$), 1.14 (3H, d, J=7.0 Hz, $Me_2$), 1.11(3H, d, J=7.0 Hz, $Me_4$), 1.00 (3H, d, J=3.1 Hz, $Me_{20}$), 0.99 (3H, d, J=3.3 Hz, $Me_{10}$), 0.96–0.90 (21H, m, $Me_{18}$+2×SiC($C\underline{H}_3$)$_3$), 0.88 (3H, d, J=6.6 Hz,$Me_{12}$), 0.83 (9H, s, SiC($C\underline{H}_3$)$_3$), 0.73 (3H, d, J=6.7 Hz, $Me_{16}$), 0.10 & 0.08 & 0.04 & 0.03 & 0.03 & 0.01 (6×3H, 3×Si($C\underline{H}_3$)$_2$); $^{13}C$ NMR (100.6 MHz, $CDCl_3$) δ 212.9, 175.9, 156.9, 136.0, 133.7, 132.1, 131.9, 131.3, 129.8, 129.6, 117.9, 80.6, 78.7, 76.8, 73.6, 64.9, 62.1, 61.3, 54.7, 53.1, 51.7, 49.0, 45.1, 44.9, 37.9, 37.1, 36.2, 35.9, 35.0, 34.4, 30.0, 29.1, 26.26, 26.24, 25.97, 23.0, 18.51, 18.5, 18.43, 18.14, 17.43, 16.44, 13.5, 10.99, 10.1, −3.29, −3.4, −3.5, −3.9, 4.1, −4.4; m/z (ESI+) 1017 (100 (MNa$^+$)).

b) Preparation of (2R,3S,4S,5S,7S,8Z, 10S,11S,12S,13Z, 16S,17R,18R,19S,20S, 21E)-19-[(aminocarbonyl)oxyl]-3, 11,17-tris[[(1,1-dimethylethyl)dimethylsilyl]oxy]-5,7-dihydroxy-N-methoxy-N, 2,4,10,12,14,16,18,20-nonamethyl-8,13,21,23-tetracosatetraenamide

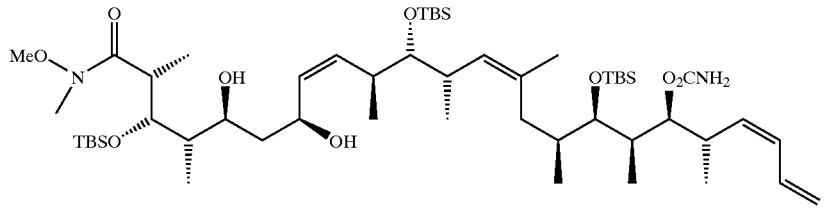

To a solution of 1.02 g (3.9 mmol) of tetramethylammonium triacetoxyborohydride in 2.2 mL of anhydrous acetonitrile is added 2.2 mL of anhydrous acetic acid and the mixture is stirred at ambient temperature for 30 min. The mixture is then cooled to −29° C. and to the cooled mixture is added a solution of 450 mg (0.453 mmol) of the compound prepared in a) above in 1 mL of anhydrous acetonitrile. The resultant mixture is then stirred at −29° C. for 18 hours, after which time the reaction is quenched with 2 mL of 0.5N aqueous sodium potassium tartrate. The mixture is then allowed to warm slowly to ambient temperature, after which it is diluted with methylene chloride and washed with saturated sodium bicarbonate. The aqueous layer is then extracted four times with methylene chloride. The combined organic layers are then washed with brine, dried with sodium sulfate and concentrated in vacuo. The resultant residue is then purified by flash chromatography (Biotage, silica gel, gradient 10–30% ethyl acetate/hexane) to yield the desired compound as a white solid.

$[\alpha]$+29.75 degree (c=0.87, $CH_2Cl_2$); $^1H$ NMR (499.87 MHz, $CDCl_3$) δ 6.60 (1H, ddd, J=16.8, 10.5, 10.5 Hz, $H_{23}$), 6.02 (1H, t, J=11.0, $H_{22}$), 5.48 (1H, dd, J=10.0, 9.8 Hz, $H_9$), 5.37 (1H, dd, J=10.6, 11.2 Hz, $H_{21}$), 5.35 (1H, dd, J=10.8, 8.5Hz, $H_8$), 5.22 (1H, d, J=15.8 Hz, $H_{24A}$), 5.12 (1H, d, J=10.2 Hz, $H_{24B}$), 4.98 (1H, d, J=10.1 Hz, $H_{13}$), 4.79 (1H, t, J=6.3 Hz, $H_7$), 4.65 (1H, t, J=5.9 Hz, $H_{19}$), 4.60–4.50 (2H, br, CON$\underline{H}_2$), 4.20 (1H, dd, J=7.7, 2.3 Hz, $H_3$), 3.92, (1H, m, $H_5$), 3.73 (3H, s, NOC$\underline{H}_3$), 3.45 (1H, br, OH-5), 3.41 (1H, dd, J=10.9, 4.7 Hz, $H_{17}$), 3.31 (1H, dd, J=5.2, 5.1 Hz, $H_{11}$), 3.18 (3H, s, $NCH_3$), 3.08 (1H, br, OH), 2.99 (1H, m, $H_{20}$), 267 (1H, m, $H_{10}$), 2.43–2.41 (2H, m), 2.11 (1H, t, J=12.3 Hz), 1.90–1.87 (2H, m), 1.76–1.58 (10H, m), 1.25 (3H, t, Me), 1.17 (3H, d, J=7.1 Hz, Me), 0.99 (3H, d, J=6.4 Hz, Me), 0.97 (3H, d, J=6.5 Hz, Me), 0.93–0.83 (30H, m, Me+3× SiC($C\underline{H}_3$)$_3$), 0.71 (3H, d, J=6.8 Hz,Me), 0.10 & 0.08 & 0.04 & 0.03 & 0.03 & 0.01 (6×3H, 3×Si($C\underline{H}_3$)$_2$). $^{13}C$ NMR (100.6MHz, $CDCl_3$) δ 156.88, 140.02, 134.19, 133.66, 132.10, 131.88, 131.40, 131.30, 131.11, 130.06, 129.79, 117.91, 115.44, 80.79, 80.69, 78.61, 78.32, 74.31, 70.68, 65.55, 61.66, 45.69, 40.38, 38.36, 37.92, 37.83, 37.29, 36.29, 35.07, 34.91, 34.45, 32.36, 29.68, 26.21, 26.12, 26.03, 25.95, 22.95, 18.52, 18.43, 18.12, 17.41, 17.07, 16.57, 13.44, 12.29, 10.32, 10.14, −3.20, −3.43, −3.96, −4.16, −4.48. m/z (ESI+) 1019 (100 (MNa$^+$)).

c) Preparation of the Title Compound

To a solution of 450 mg (0.452 mmol) of the compound prepared in b) above in 56 mL of tetrahydrofuran is added 56 mL of an aqueous solution of 4N hydrochloric acid. The resultant solution is then stirred at room temperature for 24 hours, 10 mL of methanol is then added, and this solution is then stirred for an additional 24 hours at room temperature. To the solution is then added 50 mL of ethyl acetate, followed by the addition of sodium bicarbonate at 0° C. to a pH of 8. The organic solution is then washed with brine. The aqueous layer is then extracted three times with 30 mL portions of ethyl acetate, and the combined extracts are dried over sodium sulfate. Filtration and concentration followed by flash chromatography employing an eluent mixture of 50% methylene chloride in ethyl acetate initially and then 100% ethyl acetate yields the desired compound, m.p. 122°–124° C.

$[\alpha]+22.0°$ (c=1.41, MeOH); $^1$H NMR (500 MHz, CD$_3$OD) δ 6.68 (1H, ddd, J=16.7, 10.9, 10.5 Hz, H$_{23}$), 6.08 (1H, t, J=11.0, Hz, H$_{22}$), 5.62 (1H, t, J=10.1 Hz, H$_9$), 5.48 (1H, t, J=10.7, H$_{21}$), 5.39 (1H, dd, J=10.7, 8.8 Hz, H$_8$), 5.28(1H, d, J=16.9, Hz, H$_{24A}$), 5.17 (1H, d, J=10.2 Hz, H$_{24B}$), 4.96 (1H, d, J=10.1 Hz, H$_{13}$), 4.86 (2H, br, CONH$_2$), 4.60 (1H, t, J=10.4 Hz, H$_7$), 4.58 (1H, t, J=9.7 Hz, H$_{19}$), 3.66 (1H, t, 3.9), 3.22 (1H, dd, J=7.9, 3.3 Hz), 3.15 (1H, m), 3.12 (1H, dd, J=8.5, 3.0 Hz), 2.68 (1H, m, H$_{10}$), 2.64 (1H, m, H$_2$), 2.33 (1H, m, H$_{12}$), 1.90 (5H, m), 1.63 (1H, m), 1.62 (3H, s, Me), 1.55–1.50 (1H, m), 1.26 (3H, d, J=7.4 Hz, Me), 1.07(6H, d, J=6.8 Hz, 2Me), 1.01 (3H, d, J=6.8 Hz, Me), 0.9 (3H, d, J=6.6 Hz, Me), 0.89 (3H, d, J=6.8 Hz,Me), 0.79 (3H, d, J=6.3 Hz, Me). $^{13}$C NMR (100.6 MHz, CDCl$_3$) δ 176.8, 160.33, 134.17. 133.92, 133.88, 133.59, 133.28, 131.59, 131.00, 118.80, 80.66, 80.22, 78.48, 76.48, 73.66, 63.70, 44.56, 42.60, 38.79, 37.71, 36.92, 36.77, 36.69, 34.97, 34.62, 23.45, 19.73, 18.25, 18.11, 16.05,15.84, 13.27, 9.44. m/z (ESI+) 594 (100 (M+1$^+$)).

What is claimed is:

1. A process for preparing a compound of formula V

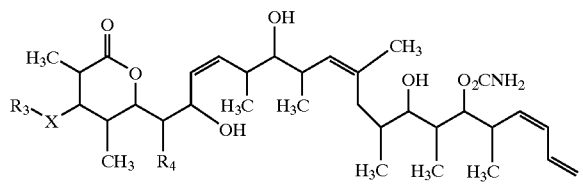

which comprises, in a first step, coupling a ketone compound of formula I

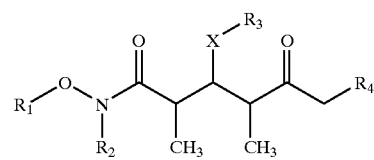

with an aldehyde compound of formula II

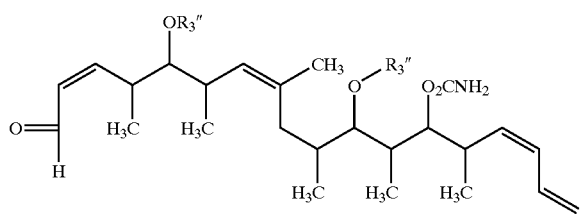

in the presence of a dialkyl boron halide or triflate, an amine base, and a polar organic solvent to obtain a β-hydroxyketone of formula III

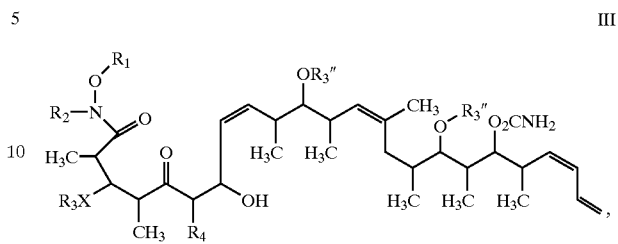

in a second step, reducing the ketone compound obtained in the first step by treating it with a borohydride reagent in a polar organic solvent and a protic solvent to obtain a 1,3-diol of formula IV and, in a third step, lactonizing and deprotecting the acid labile hydroxyl protecting groups of the 1,3 diol obtained in the second step by treating it with a hydrogen halide dissolved in a polar solvent or mixture of solvents to obtain the desired compound of formula V, where R$_1$ is (C$_{1-6}$) alkyl, benzyl or an acid labile hydroxyl protecting group; R$_2$ is (C$_{1-6}$) alkyl or benzyl; R$_3$ is hydrogen, (C$_{1-6}$) alkyl, benzyl, C(O)(C$_{1-12}$) alkyl, C(O)Ph, C(O)O(C$_{1-12}$) alkyl, C(O)OPh, C(O)NH(C$_{1-12}$) alkyl, C(O)NHPh or an acid labile hydroxyl protecting group; R$_3$" is an acid labile hydroxyl protecting group; R$_4$ is hydrogen or methyl; and X is O, NH, NCH$_3$, S or CH$_2$, with the proviso that when X is O and R$_3$ is an acid labile hydroxyl protecting group in the compound of formula I, the "—X—R$_3$" moiety in the compound of formula V is —OH.

2. A process according to claim 1 wherein the coupling step is carried out in the presence of β-chlorodiisopinocamphenylborane, triethylamine and diethyl ether, at a temperature of between –78° C. and –20° C.

3. A process according to claim 1 wherein the reduction step is carried out in the presence of tetramethylammonium triacetoxyborohydride, acetonitrile and acetic acid, at a temperature of between –40° C. and –10° C.

4. A process according to claim 1 wherein the lactonization and deprotection of the acid labile hydroxyl protecting groups step is carried out in the presence of aqueous hydrogen chloride, methanol and tetrahydrofuran, at a temperature of between –20° C. and 40° C.

5. A compound of formula I:

where R$_1$ is (C$_{1-6}$) alkyl, benzyl, or an acid labile hydroxyl protecting group;

R$_2$ is (C$_{1-6}$) alkyl, or benzyl;

R$_3$ is hydrogen, (C$_{1-6}$) alkyl, benzyl, C(O)(C$_{1-12}$) alkyl, C(O)Ph, C(O)O(C$_{1-12}$)alkyl, C(O)OPh, C(O)NH (C$_{1-12}$)alkyl, C(O)NHPh, or an acid labile hydroxyl protecting group;

R$_4$ is hydrogen or methyl; and

X is O, NH, NCH$_3$, S or CH$_2$.

6. A compound according to claim 5 of formula Ia:

where each of R$_1$' and R$_2$' is (C$_{1-6}$) alkyl;

X' is O, or CH$_2$; and

R$_3$ and R$_4$ are as defined in claim 5.

7. A compound according to claim 6 of formula Ib:

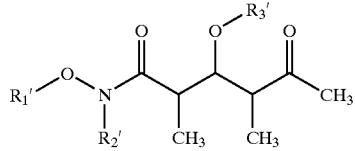

Ib where R₃' is (C₁₋₆)alkyl, C(O)(C₁₋₁₂)alkyl, benzyl, C(O)O (C₁₋₁₂)alkyl, or an acid labile hydroxyl protecting group; and R₁' and R₂' are as defined in claim 6.

8. A compound according to claim 7 of formula Ic:

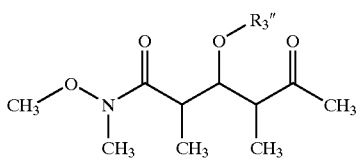

Ic where R₃" is an acid labile hydroxyl protecting group.

9. A compound according to claim 8 which is (2R,3S, 4R)-3-[[(1,1-dimethylethyl)dimethylsilyl]oxy]-N-methoxy-N,2,4-trimethyl-5-oxo-hexanamide having the formula

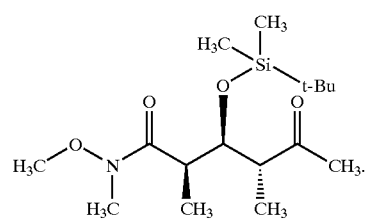

10. A process for preparing a compound of formula I according to claim 5 which comprises, in a first step, addition of a methyl or ethyl organometallic reagent to an aldehyde of formula VI

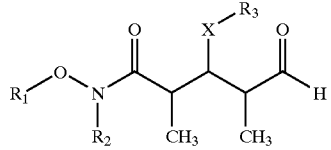

VI in the presence of a polar organic solvent to obtain an alcohol of formula VII

VII and, in a second step, oxidizing the alcohol compound prepared in the first step by treating it with an oxidant and a base in a polar organic solvent to obtain the desired compound of formula I, wherein R₁, R₂, R₃, R₄ and X are as defined in claim 5.

11. A process according to claim 10 wherein the addition step is carried out in the presence of methylmagnesium bromide and diethyl ether, at a temperature of between −78° C. and 40° C.

12. A process according to claim 10 wherein the oxidation step is carried out in the presence of sulfur trioxide-pyridine complex, triethylamine and dichloromethane, at a temperature of between −78° C. and 40° C.

13. A compound of formula III:

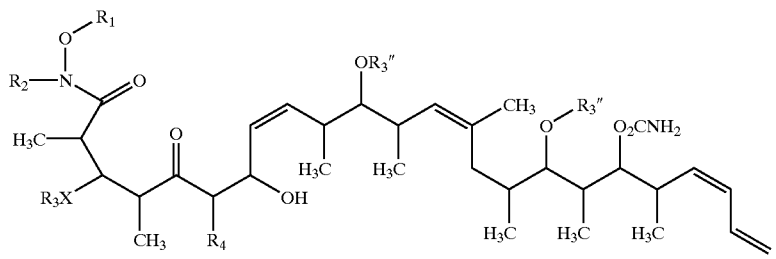

III where R₁ is (C₁₋₆) alkyl, benzyl, or an acid labile hydroxyl protecting group;

R₂ is (C₁₋₆) alkyl, or benzyl;

R₃ is hydrogen, (C₁₋₆) alkyl, benzyl, C(O)(C₁₋₁₂) alkyl, C(O)Ph, C(O)O(C₁₋₁₂)alkyl, C(O)OPh, C(O)NH (C₁₋₁₂)alkyl, C(O)NHPh, or an acid labile hydroxyl protecting group;

R₄ is hydrogen or methyl;

X is O, NH, NCH₃, S or CH₂; and each R₃" is an acid labile hydroxyl protecting group.

14. A compound according to claim 13 which is (2R,3S, 4R,7S,8Z,10S,11S,12S,13Z, 16S,17R,18R,19S,20S,21E)-19-[(aminocarbonyl)oxy]-3,11,17-tris[[(1,1-dimethylethyl)-dimethylsilyl]oxy]-7-hydroxy-N-methoxy-N, 2,4,10,12,14, 16,18,20-nonamethyl-5-oxo-8,13,21,23-tetracosatetraenamide having the formula

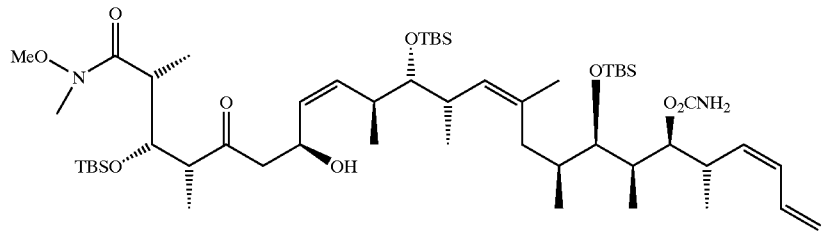

15. A compound of formula IV:

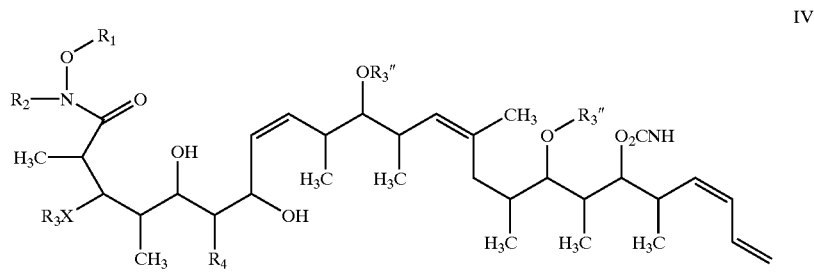

where $R_1$ is $(C_{1-6})$ alkyl, benzyl, or an acid labile hydroxyl protecting group;

$R_2$ is $(C_{1-6})$ alkyl, or benzyl;

$R_3$ is hydrogen, $(C_{1-6})$alkyl, benzyl, $C(O)(C_{1-12})$ alkyl, $C(O)Ph$, $C(O)O(C_{1-12})$alkyl, $C(O)OPh$, $C(O)NH(C_{1-12})$alkyl, $C(O)NHPh$, or an acid labile hydroxyl protecting group;

$R_4$ is hydrogen or methyl;

X is O, NH, $NCH_3$, S or $CH_2$; and each $R_3''$ is an acid labile hydroxyl protecting group.

16. A compound according to claim 15 which is (2R,3S, 4S, 5S,7S,8Z,10S,11S,12S,13Z,16S, 17R,18R,19S,20S, 21E)-19-[(aminocarbonyl)oxy]-3,11,17-tris[[(1,1-dimethylethyl)dimethylsilyl]oxy]-5,7-dihydroxy-N-methoxy-N,2,4,10,12,14,16,18,20-nonamethyl-8,13,21,23-tetracosatetraenamide having the formula

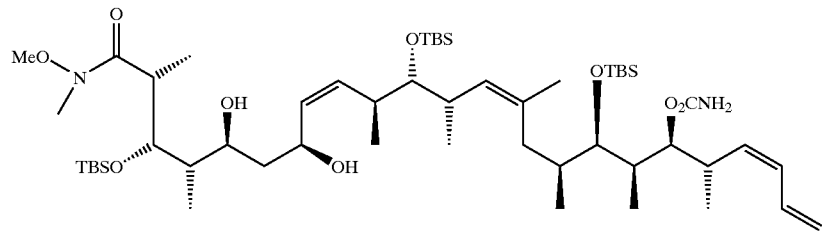

* * * * *

UNITED STATES PATENT AND TRADEMARK OFFICE
CERTIFICATE OF CORRECTION

PATENT NO.    : 6,506,910 B1                                      Page 1 of 1
DATED         : January 14, 2003
INVENTOR(S)   : Frederick Ray Kinder, Jr.

It is certified that error appears in the above-identified patent and that said Letters Patent is hereby corrected as shown below:

Column 12,
Line 19, should read:

-- of formula IV

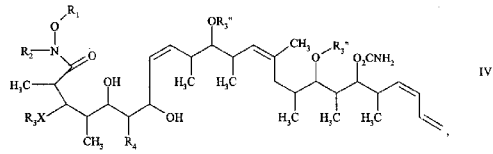

--

Line 51, should read:

-- 5. A compound of formula I:

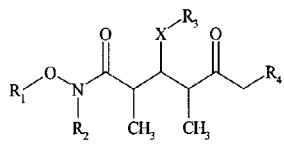

--

Line 62, should read:

-- 6. A compound according to claim 5 of formula Ia:

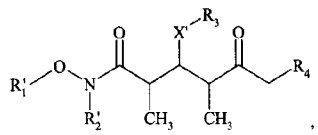

, --

Signed and Sealed this

Twenty-ninth Day of July, 2003

JAMES E. ROGAN
*Director of the United States Patent and Trademark Office*